(12) United States Patent
Que et al.

(10) Patent No.: US 6,858,135 B2
(45) Date of Patent: Feb. 22, 2005

(54) HYDROPHILIC MONOLITHIC COLUMNS FOR SEPARATION OF SACCHARIDE MIXTURES

(75) Inventors: Amy H. Que, Chesterfield, MO (US); Milos V. Novotny, Bloomington, IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 4 days.

(21) Appl. No.: 10/634,058

(22) Filed: Aug. 4, 2003

(65) Prior Publication Data

US 2004/0094481 A1 May 20, 2004

Related U.S. Application Data

(60) Provisional application No. 60/426,919, filed on Nov. 15, 2002.

(51) Int. Cl.$^7$ .............................................. B01D 15/08
(52) U.S. Cl. .............................. 210/198.2; 210/502.1; 210/635; 210/656
(58) Field of Search ................................ 210/635, 656, 210/198.2, 659, 502.1

(56) References Cited

U.S. PATENT DOCUMENTS

| | | | | |
|---|---|---|---|---|
| 5,647,979 A | * | 7/1997 | Liao et al. ............... | 210/198.2 |
| 5,935,429 A | * | 8/1999 | Liao et al. ............... | 210/198.2 |
| 6,066,258 A | * | 5/2000 | Gjerde et al. .............. | 210/635 |
| 6,372,130 B1 | | 4/2002 | Gjerde et al. ............ | 210/198.2 |
| 2004/0071968 A1 | * | 4/2004 | Kyrlidis et al. ............. | 428/408 |

OTHER PUBLICATIONS

Mechref, Y. et al. , "Structural Investigations of Glycocojungates at High Sensitivity", Chem. Rev., 102: 321–369 (2002).

Mechref, Y. et al., "Mass Spectrometric Mapping and Sequencing of N–Linked Oligosaccharides Derived from Submicrogram Amounts of Glycoproteins", Anal. Chem., 70:455–463 (1998).

Hong, M. et al., "High–Resolution Studies of Hyaluronic Acid Mixtures through Capillary Gel Electrophoresis", Anal. Chem., 70:568–573 (1998).

Huang, Y. et al., "Microscale Nonreductive Release of O–Linked Glycans for Subsequent Analysis through MALDI Mass Spectrometry and Capillary Electrophoresis", Anal. Chem., 73:6063–6069 (2001).

Huang, Y. et al., "Matrix–assisted Laser Desorption/Ionization Mass Spectrometry Compatible β–elimination of O–linked Oligosaccharides", Rapid Commun. Mass Spectrom., 16:1199–1204 (2002).

Que, A. et al., "Analysis of Bile Acids and Their Conjugates by Capillary Electrochromatography/Electrospray Ion Trap Mass Spectrometry", Anal.Chem., 72:2703–2710 (2000).

Que, A. et al., "Steroid Profiles Determined by Capillary Electrochromatography, Laser–induced Fluorescence Detection and Electrospray–Mass Spectrometry", Journal of Chromatography, 887:379–391 (2001).

Que, A. etal., "Separation of Neutral Saccharide Mixtures with Capillary Electrochromatography using Hydrophilic Monolithic Columns", Anal. Chem., 74:5184–5191 (2002).

Palm, A. et al., "Macroporous Polyacrylamide/Poly(ethylene glycol) Matrixes as Stationary Phases in Capillary Electrochromatography", Anal. Chem., 69:4499–4507 (1997).

(List continued on next page.)

Primary Examiner—Ernest G. Therkorn
(74) Attorney, Agent, or Firm—Barnes & Thornburg LLP (57) ABSTRACT

Polar, monolithic CEC columns having an amine and/or cyano functional stationary phase are used to separate complex mixtures of saccharides. Using the positive-ion mode of detection for neutral saccharides, detection conditions were optimized to low-femtomole sensitivities with the use of an ion trap mass spectrometer. The described column technology provides a universal system for separating a wide range of carbohydrates: mono- and oligosaccharides with the intact reducing end, as well as saccharide alditols.

12 Claims, 9 Drawing Sheets

OTHER PUBLICATIONS

Que et al., "Structural Characterization of Neutral Oligosaccharide Mixtures Through a Combination of Capillary Electrochromatography and Ion Trap Tandem Mass Spectrometry", *Anal. Bioanal. Chem.*, 375:599–608 (2003).

Que. et al., "Coupling Capillary Electrochromatography with Electrospray Fourier Transform Mass Spectrometry for Characterizing Complex Oligosaccharide Pools", *Anal. Chem.*, 75:1684–1690 (2003).

* cited by examiner

HYDROPHILIC MONOLITHIC COLUMNS FOR SEPARATION OF SACCHARIDE MIXTURES

This application claims priority under 35 U.S.C. § 119(e) to U.S. Provisional Application Ser. No. 60/426,919, filed on Nov. 15, 2002, the disclosure of which is hereby incorporated by reference herein.

GOVERNMENT RIGHTS

Research relating to this invention was supported in part by the U.S. Government under Grant No. GM24349 awarded from the National Institute of Health. The U.S. Government may have certain rights in this invention.

FIELD OF INVENTION

This invention relates to hydrophilic monolithic columns for use in chromatography. More particularly, this invention is directed to hydrophilic monolithic columns having a macroporous polymeric stationary phase, such as a column matrix, having unique properties for the separation of saccharide mixtures.

BACKGROUND OF THE INVENTION

Many biologically interesting proteins are glycosylated at their asparagine, serine, and threonine residues. Glycosylation has now been recognized as being more ubiquitous and structurally varied than all other types of post-translational modifications combined. While glycoproteins are being increasingly implicated to be crucial to processes as diverse as cellular adhesion, egg fertilization, targeting aging cells, etc., very little is known about the underlying molecular basis of sugar-sugar and sugar-protein interactions. The extreme complexity of glycan structures, multiple substitutions (microheterogeneity) at glycosylation sites, and the structural diversity associated with the protein backbone itself thus represent an enormous task for analytical structural studies.

Traditionally, a complete structural analysis of the glycan structures, including determination of the carbohydrate sequence and sugar linkage forms, has been a tedious, multitechnique task, often necessitating milligram to gram quantities of material. To progress from this situation, it is first essential to have a sensitive end-measurement methodology.

Modern mass spectrometry (MS), featuring most prominently the matrix-assisted laser desorption/ionization (MALDI) and electrospray ionization (ESI) methodologies, has now become prominent in structural elucidation of complex carbohydrates. Mechref, Y. et al., *Chem. Rev.* 102, 321–370 (2002); Dell, A. et al., *Science* 291, 2351–2356 (2001). During studies on complex carbohydrate mixtures (e.g., various glycan pools released from glycoproteins), a separation in time and space prior to MS, in either on-line or off-line modes, appears necessary. While MS of separated glycans is inherently informative of the molecular details such as sequence and linkage, certain chromatographic and electromigration principles can also readily resolve various isomeric structures.

The gradual development of high-performance liquid chromatography (HPLC) over the last three decades, with an ever-expanding range of new sorption materials, has provided some viable alternatives in carbohydrate separations. Hydrophilic interaction and adsorption chromatography, reversed-phase HPLC, anion-exchange chromatography, and lectin affinity column chromatography have all been used (Mechref, Y. et al., *Chem. Rev.* 102, 321–370 (2002)), albeit in different analytical applications and detection modes and, in some cases, with the use of sample derivatization.

The HPLC carbohydrate methodologies developed to date are rarely suitable for a coupling to MS: the silica-based hydrophilic interaction and adsorption columns suffer from lack of reproducibility and short lifetimes, while the additional HPLC modes requiring strong buffers and alkaline conditions are not easily adjustable to MS operation. Moreover, the extraordinary complexity of most glycan mixtures presents a major challenge to the ordinary HPLC with a limited resolving power. The modern capillary electromigration techniques, such as capillary zone electrophoresis (CZE), micellar electrokinetic chromatography (MEKC), and capillary electrochromatography (CEC), were recently shown to provide unprecedented resolution of complex oligosaccharide mixtures. Mechref, Y. et al., *Chem. Rev.* 102, 321–370 (2002); Novotny, M., *Methods Enzymol.* 271, 319–347 (1996); Hong, M. et al., *Anal. Chem.* 70, 568–573 (1998). However, CZE and MEKC also suffer from certain analytical disadvantages, namely, (a) incompatibility of their separation buffers and mobile phases with MS, (b) limited options for sample preconcentration, and (c) on occasion, a lack of separation selectivity. Due to its potential for variations in the design of suitable mobile-phase/stationary phase combinations, CEC is perhaps the most suitable electromigration alternative for coupling with MS methodologies.

SUMMARY OF THE INVENTION

Hydrophilic (polar), monolithic chromatographic columns are provided for separation of complex mixtures of saccharides. The columns have, for example, a polyfunctional polyacrylamide gel as the column matrix, i.e. the stationary phase. The polyacrylamide gel comprises either amino or cyano functional groups bonded to the gel. The presence of the amino or cyano functionality allows for the efficient separation of saccharide mixtures, particularly those mixtures composed of mono-, di-, and oligosaccharides with the intact reducing end, as well as saccharide alditols and the anomers formed due to mutarotation. The polyacrylamide gel can also comprise a charge functional group. The charge functional group is a group that is capable of maintaining either a positive or negative charge over a broad pH range, affecting the flow of the mobile phase through the column.

A method for using the columns to separate complex mixtures of saccharides is also provided. The methods comprise the steps of introducing a sample of a saccharide mixture to the columns of the present invention, inducing flow of a mobile phase to produce a column effluent and detecting the separated saccharides in the column effluent. In one preferred embodiment the column is a capillary electrochromatographic column and the flow of mobile phase is induced by applying an electrical potential across the column. The saccharide mixture can contain mono-, di-, oligosaccharides or mixtures thereof. Mixtures of oligosaccharides may be obtained by cleavage from glycoproteins. The mobile phase is organic based and allows for easy coupling of the columns to mass spectrometry instruments.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which.

DETAILED DESCRIPTION OF THE INVENTION

Hydrophilic (polar), monolithic chromatography columns that are used to effectively separate complex mixtures of saccharides with the use of an aqueous organic mobile phase are provided. The columns have a modified polyfunctional polyacrylamide gel as the stationary phase. The polyacrylamide gel further comprises either an amino or cyano functionality bonded to the gel. The presence of the amino or cyano functionality allows for the efficient separation of saccharide mixtures, particularly those mixtures composed of mono- and oligosaccharides with the intact reducing end, as well as saccharide alditols and the anomers formed due to mutarotation. In one embodiment, columns particularly adapted for capillary electrochromatography (CEC), the polyacrylamide gel component also comprises charge functional groups. A charge functional group is a moiety that is capable of maintaining either a positive or negative charge over a broad pH range, affecting the electromotive-induced flow of the mobile phase through the column.

Separation of saccharides on the present column is based on H-bonding and dipole-dipole interactions with functional groups on the stationary phase and not by size exclusion. Therefore, the polyacrylamide gel has sufficient cross-linking to provide a mechanically stable stationary phase as well as large pores or spaces to provide a pathway for the saccharides through the column. The pores or spaces are integrated into the gel by including a compound or compounds in the monomer mixture during polymerization, where the compounds are chemically inert to the both the polyacrylamide gel and the reactants that form the gel. The "filler" compound(s) is then washed from the polyacrylamide gel thereby providing the porous structure. There is also the consideration of the size and/or volume of the pores as well as the number of pores. The molecular size of the "filler" compound should be large enough so that the pores formed allow a pathway for the saccharides so that separation is not based on size exclusion. Conversely, the compound should not be so large that the pores compromise the structural integrity of the polyacrylamide gel. In an exemplary embodiment, the compound is polyethylene glycol (PEG). PEG having a molecular weight of 7,500 to 20,000 produces an optimal pore size in the polyacrylamide stationary phase, i.e. the polyacrylamide gel. The amount of PEG present during polymerization of the gel can be from about 1% (w/v) to about 5% (w/v).

In another embodiment, the stationary phase polyacrylamide gel of the present columns has amino and/or cyano functional groups covalently attached to the gel. The amino-functional group can be a primary, tertiary or secondary amine. These functional groups interact with the hydroxyl moieties of the saccharides and influence, along with the composition of the mobile phase, the elution volumes for individual saccharides. The concentration of amino- or cyano-functional groups attached to the gel will affect the elution volume of each saccharide. The concentration of the amino or cyano functional group attached to the polyacrylamide gel can be adjusted to give optimal separation of complex saccharide mixtures.

In yet another embodiment, a charge ligand is also covalently incorporated into the polyacrylamide gel stationary phase, i.e. the polyacrylamide gel. The charge ligand comprises a functional group that is capable of maintaining a charge. The charge ligand helps to move the mobile phase through the column when a suitable potential is applied. Increasing the concentration of charge ligand typically increases the rate of flow of the mobile phase through the column. Conversely, decreasing the concentration of the charge ligand decreases the flow rate of the mobile phase for a given applied potential. Therefore, the concentration of the charge ligand and the electrical field strength can be adjusted to give a flow rate that produces an optimal separation of the saccharides on the column of the present invention. The charge ligand can either have a negative charge or a positive charge. In an exemplary embodiment, the charge ligand can maintain a charge in an aqueous system over a broad pH range. Exemplary charge ligands are sulfonic acids or quaternary amines.

The amino and/or cyano functional groups and the charge ligand are covalently incorporated into the polyacrylamide gel during polymerization of a mixture of monomers to form the gel. The polyacrylamide gel is formed by the polymerization of a monomer mixture comprising acrylamide, bisacrylamide, a polymerizable charge ligand, and a polymerizable cyano or amino compound. The polymerizable charge ligand has the formula RX where X is functional group capable of maintaining a charge and R is an olefin functional group capable of free radical-propagated polymerization. The amount of RX can be chosen to give the desired flow rate of the mobile phase. In an illustrative example, the amount of RX in the monomer mixture is from about 5 mol % to about 40 mol % based on the total monomer components. In another illustrative example, RX is either vinylsulfonic acid or [2-(acryloyloxy)-ethyl] triethylammonium methyl sulfate.

The polymerizable cyano compound for use in the monomer mixtures for preparing stationary phases for the present columns has the formula R'CN where R' is an olefin functional group capable of free radical-propagated polymerization. An illustrative example of R'CN is 2-cyanoethyl acrylate. The polymerizable amino compound has the formula R"N(R$_1$)(R$_2$) where R$_1$ and R$_2$ are each independently H or a C$_1$–C$_6$ alkyl and R" is an olefin functional group capable of free radical-propagated polymerization. An illustrative example of R"N(R$_1$)(R$_2$) is 3-amino-1-propanol vinyl ether. The amount of polymerizable cyano or amino compound will be chosen to give the best separation of the saccharides in the mixture. The amount of cyano or amino compound in the monomer mixture can be from about 10 mol % to about 60 mol % based on the total monomer components. In an exemplary embodiment the amount of cyano or amino compound is from about 30 mol % to about 40 mol % based on the total monomer components.

In one embodiment, the stationary phase is formed in situ. The monomer mixture is prepared including a radical initiator and is then placed in the column as a liquid. The monomer mixture is then allowed to remain in the column until it polymerizes. The amount of radical initiator should not be so great that polymerization begins to occur before the monomer mixture is placed in the column. After polymerization, the resulting polyacrylamide gel can be washed to remove the "filler" compound to form the pores. The column can then be equilibrated to be used in methods to separate mixtures of saccharides.

Methods for using the columns of the present invention to separate saccharide mixtures are also provided. The methods comprise the steps of introducing a sample of a saccharide mixture to the columns of the present invention, applying a voltage potential across the column to obtain sufficient flow of a mobile phase to produce a column effluent and detecting the separated saccharides in the column effluent. The saccharide mixture can contain mono-, di-, oligosaccharides or mixtures thereof. Mixtures of oligosaccharides can be obtained by cleavage from glycoproteins, glycolipids, or other biological moieties.

A sample of the saccharide mixture is introduced to a column of the present invention which as been equilibrated with a mobile phase. The sample is usually injected into the column by applying a voltage of about 1 kV to about 4 kV for a period of about 10 seconds. After the sample is introduced to the column, a voltage potential is applied to the column, where the voltage potential is sufficient to cause flow of the mobile phase to produce a column effluent. The mobile phase is chosen with two considerations, namely, optimal separation of the saccharides and compatibility with the method for detecting the saccharides in the column effluent. For example, if the detection method is MALDI or electrospray mass spectroscopy, the mobile phase should contain an organic solvent and a minimal amount of salts. It has been found that for mass spectroscopy detection of the saccharides a mobile phase comprising acetonitrile, water and ammonium formate buffer (240 mM, pH 3.0) works well. For example, the amount for formate buffer is 1% and the amount of acetonitrile can be from about 50 vol % to about 99 vol %. The amount of acetonitrile in the mobile phase will depend on the composition of the saccharide mixture and the amount of separation desired. For example, for separating non-reducing sugars, the amount of acetonitrile can be from about 50 vol % to about 99 vol %. For the separation of saccharide anomers form from mutarotation, better separation is obtained when the acetonitrile is from about 80 vol % to about 99 vol %. It is routine in the art to adjust the amount of acetonitrile in the mobile phase to give the desired separation.

Figure 1:
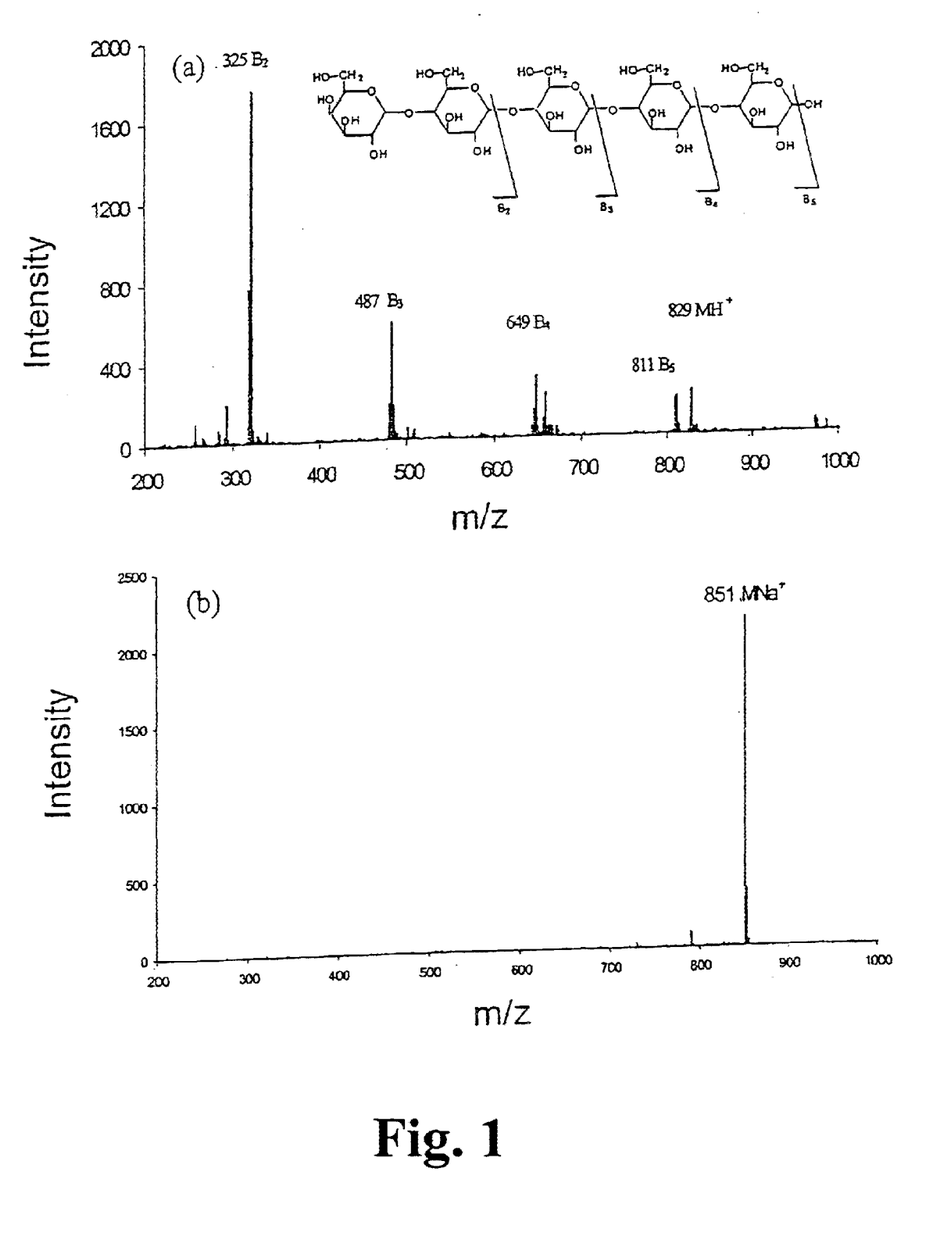
FIG. 1A is a mass spectra for maltopentaose with sheath liquid conditions of 1% fortnic acid (v/v) in a mixture of acetonitrile/water (50:50, v/v)
FIG. 1B is a mass spectra for maltopentaose with sheath liquid conditions of 1% formic acid (v/v)+1 mM sodium acetate in a mixture of acetonitrile/water (50:50, v/v)

In another embodiment, the saccharides in the column effluent are detected. There are known methods in the art for detecting saccharides, including mass spectroscopy, post-column labeling and detection by UV or fluorescence, electrochemical detection as well as other methods. Mass spectroscopy, however, is the most sensitive method and allows both detection and characterization of the saccharides in the column effluent. When mass spectroscopy is used to analyze the saccharides in the column effluent, it may be advantageous to add a sheath liquid to the column effluent before mass spec analysis. The addition of the sheath fluid allows the consistent formation of molecular ions for detection, especially when the sample contains a neutral saccharide. For example, the addition of a sheath liquid comprising 1% formic acid and 1 mM sodium acetate in acetonitrile/water (50:50, v/v) allowed the formation of molecular ions in a sample having maltopentaose (FIGS. 1A and 1B).

The foregoing and other aspects of the invention may be better understood in connection with the following example, which is presented for purposes of illustration and not by way of limitation.

EXAMPLES

Chemicals. Acrylamide and N,N'-methylenebisacrylamide were purchased from Bio-Rad Laboratories (Hercules, Calif.). Ammonium persulfate, N,N,N',N'-tetramethylenediamine (TEMED), (3-methacryloxypropyl)trimethoxysilane (Bind-Silane), poly(ethylene glycol) (PEG, MW 10 000), and all carbohydrate standards were purchased from Sigma (St. Louis, Mo.). [2-(Acryloyloxy)ethyl]-trimethylammonium methyl sulfate (2-AETMA, 80 wt %), 3-amino-1-propanol vinyl ether (APVE, 96%), vinylsulfonic acid (sodium salt, 25% (v/v)), 2-cyanoethyl acrylate (CEA), and formamide were purchased from Aldrich (Milwaukee, Wis.). Dextrin 20 was purchased from Fluka (Buchs, Switzerland).

Reduction of Disaccharide Aldoses to Alditols. Aliquots of 4.00 mg of disaccharide aldoses (lactose, maltose, cellobiose, melibiose) were dissolved and incubated in 0.1 mL of 1 M sodium borohydride (freshly made in 1 N NaOH solution) for 1–2 h. The reaction solution was neutralized with a strong cation-exchange resin (H$^+$ form, Dowex 50Wx8-400, Sigma), until pH 7 was reached, to remove the excess amount of Na$^+$ in the solution. The solution was then filtered to remove the resin. Boric acid was removed in the form of volatile methyl borate by coevaporation with methanol. The alditols were recovered by evaporation of solvent to dryness and redissolved in 100.0 µL of deionized water.

Column Preparation. Activation of Capillary Tubing. Fused silica tubing (Polymicro Technologies, Phoenix, Ariz.) with a 100-µm i.d. and a 160-µm o.d. was used to make all CEC columns. The inner wall of the capillary tubing was first treated with 1 M sodium hydroxide (statically, 2×15 min). Following a flushing with distilled water, the capillary was filled with 0.1 M hydrochloric acid and treated twice for 15 min (statically, 2×15 min). The estimated volume of hydrochloric acid used was about 20–50 µL. The capillary was rinsed subsequently with distilled water for 30 min. A 50% (v/v) Bind-Silane (bifunctional reagent) solution in acetone was then introduced into the capillary and left inside it for 2×20 min. Finally, the capillary was rinsed with acetone and water.

Aminoalkyl-phase CEC columns, containing 5% total monomer concentration (g/ml) (T), 60% total cross-linker concentration (g/g) (C), 3% (w/v) PEG, 30 mol % AETMA, and 30 mol % APVE (according to Hjertén's designation; Hjertén, S., Arch. Biochem. Biophys. (Suppl. 1), 147–151 (1962)), were prepared according to the procedures described previously. Que, A. H. et al., Anal. Chem. 72, 2703–2710 (2000). Eight milligrams of acrylamide, 30 mg of bis-acrylamide, 9.9 µL of APVE, 24.0 µL of AETMA, and 30 mg of PEG were dissolved in 0.5 mL of formamide/0.5 mL of 100 mM Tris-150 mM boric acid (pH 8.2). During polymerization, 2 µL of 20% (v/v) TEMED and 2 µL of 20% ammonium persulfate were added to 0.5 mL of the above monomer solution. The polymerization proceeded overnight at room temperature. To remove excess amount of reagents, the capillary column was then washed for 2–4 h with an appropriate buffer, and purged with compressed nitrogen gas at 100–200 psi. The column was then conditioned by gradually applying electrical force in an appropriate operating buffer. The well-conditioned columns were stored in the buffer before their use.

Cyano-phase CEC columns, containing 5% T, 60% C, 3% (w/v) PEG, 30 mol % CEA, and 10 mol % vinylsulfonic acid, were prepared as follows: 12.0 mg of acrylamide, 30 mg of bisacrylamide, 11.7 µL of CEA, 12.4 µL of vinylsulfonic acid, and 30 mg of PEG were dissolved in 0.5 mL of formamide/0.5 mL of 100 mM Tris-150 mM boric acid (pH 8.2). During the polymerization, 4 µL of 20% (v/v) TEMED and 4 µL of 40% ammonium persulfate were added to 0.5 mL of the above monomer solution. The polymerization proceeded overnight at room temperature. The column was then flushed and conditioned with phosphate buffer (5 mM, pH 3)/acetonitrile (50:50, v/v).

CEC/ESI-Ion Trap MS. The CEC/ESI-ion trap system employed in this study was described previously. Que, A. H. et al., Anal. Chem. 72, 2703–2710 (2000); Que, A. H. et al., J. Chromatogr., A 887, 379–391 (2000). The setup consisted of a 60-kV high-voltage power supply (Spellman, Plainview, N.Y.) connected to a platinum electrode in a vial containing the mobile phase. A nanospray needle (tapered needles with ~10-µm orifice were used) was prepared from fused-silica capillary (250-µm i.d., 360-µm o.d.) using a laser-based micropipet puller (Sutter, Novato, Calif.). The separation capillary was inserted into the nanospray needle so that the column outlet was placed well inside the tapered portion of the needle. A sheath liquid was used to form the circuit between the column outlet and the needle, which was maintained at +1–2 kV applied by a 30-kV high-voltage power supply (Spellman). The sheath liquid, typically containing 1% formic acid and 1 mM sodium acetate in the mixture of acetonitrile/water (50:50, v/v), was introduced at a flow rate of 0.5 µL/min through a microflow syringe pump (model µLC-50, Isco, Inc., Lincoln, Nebr.) for the efficient electrospray ionization of saccharides.

The ion trap mass spectrometer was built in our laboratory, (Que, A. H. et al., J. Chromatogr., A 887, 379–391 (2000)) using an ITMS kit obtained from Finnigan (San Jose, Calif.). Mass detection was extended using a resonant ejection technique. Kaiser, R. E. et al., Int. J. Mass Spectrom. Ion Processes 106, 79–115 (1991).

Results and Discussion

General Considerations. In choosing a proper column type from a wide range of separation principles explored in the HPLC of carbohydrates previously, it is important to consider its compatibility with the detection methods in use. For example, spectroscopic methods for carbohydrate detection typically necessitate solute derivatization, which, in turn, influences the selection of a proper mobile-phase/stationary-phase system. Likewise, high-pH ion-exchange chromatography has been a natural and widely practiced choice in conjunction with the electrochemical detection of carbohydrates. When a mass spectrometer is to be used for structural elucidation of complex glycans at high sensitivity, it seems preferable to choose a chromatographic principle permitting effective separations of underivatized carbohydrates with the least possible adverse effects of the mobile phase. These considerations have led to the choice of a polar CEC matrix in conjunction with the acetonitrile/aqueous, volatile buffer as the mobile phase.

Polar stationary phases in the HPLC of sugars are not unprecedented: siliceous materials containing amino-, cyano-, amido-, or diol-bonded phases have been used in the past, with the aminopropyl and cyano phases yielding the best results. The acetonitrile/water mixtures have been preferred as the mobile phases. While not wishing to be bound by theory, the separation mechanism is predominantly a hydrophilic partition involving hydrogen-bonding and dipole-dipole interactions between the hydroxyl groups of sugars and a polar stationary phase. It has been demonstrated previously, with bile acid conjugates (also relatively polar solutes), that combining the efficiency of CEC with a selectivity offered by a hydrophilic-phase mode can lead to excellent separations. Que, A. H. et al., Anal. Chem. 72, 2703–2710 (2000). In the present example, it has been demonstrated that both amino- and cyano-containing matrixes are effective in the separations of glycan mixtures, while permitting MS investigations of the separated components under optimum, or near-optimum, conditions. Thus, using a mass spectrometer itself as a "detector" for the separated glycans seemed appropriate.

Optimized Detection. CEC/MS offers a good alternative to MEKC/MS or CZE/MS because of its lack of interferences due to micelles or salts. Because of the need for compatibility of low CEC flow rates with MS, nano-ESI has been chosen, leading to a further exploration of the sheath-flow conditions in optimization of the interface and MS detection conditions. The main reasons for using the sheath-flow arrangement in this system have been to (a) complete a circuit for the CEC system, (b) provide a stable electrospray, and (c) ensure optimum ionization of the neutral oligosaccharides eluting from the column. An additional attribute is to enhance appearance of diagnostic fragments for different solutes through mobile-phase additives.

On the basis of previous experience with using formic acid in the CEC/MS studies of steroids and bile acids (Que, A. H. et al., Anal. Chem. 72, 2703–2710 (2000)), which provides protons for their positive-ion detection, this option was initially explored for sugars as well. Neutral and underivatized saccharides are difficult to ionize, as they are not efficiently charged by protonation or deprotonation. Adding metal ions into the sheath liquid at low concentration was generally beneficial, but the mass spectra were found to be quite sensitive to the nature and concentration of additives, so that optimization was required for both high sensitivity and acquisition of an "informative" spectrum.

Initially, 1% formic acid in acetonitrile/water (50:50 v/v) was employed in the optimization experiments. While this sheath liquid provided a low ion background and easy volatilization, the acquired mass spectra featured numerous fragments, but no molecular ions (unstable protonated molecular ions). As shown with the example of maltopentaose (FIG. 1A), fragmentation into significantly smaller ions ($B_2$ through $B_5$ series through the lowest energy channel), the glycosidic bond cleavage readily occurred under such conditions. The addition of sodium acetate (1–10 mM range) to acetonitrile/water (50:50 v/v) was found to significantly promote formation of the molecular ions for different sugars, but the background current was higher at the S/N ratio compared to the use of formic acid alone. However, when 1 mM sodium acetate was used together with 1% formic acid in a 50:50 mixture of acetonitrile and water, the sodiated molecular ions became predominant, as demonstrated in FIG. 1B with maltopentaose. Compared to either formic acid or sodium acetate used as a lone additive, the combination of both substances increased sensitivity ~5-fold. During another optimization study using maltotriose and different concentrations of formic acid and sodium acetate, similar results were obtained. While sodium ions cause better adduction than protons, the acidic medium was probably needed for a better transfer efficiency of the pseudomolecular ion from the liquid to gas phase. This optimized sheath liquid was used for all the following experiments. The detection limits for various sugars were around 40–50 fmol in the total ion current (TIC) mode and around 1–2 fmol for selected ions.

Figure 2:
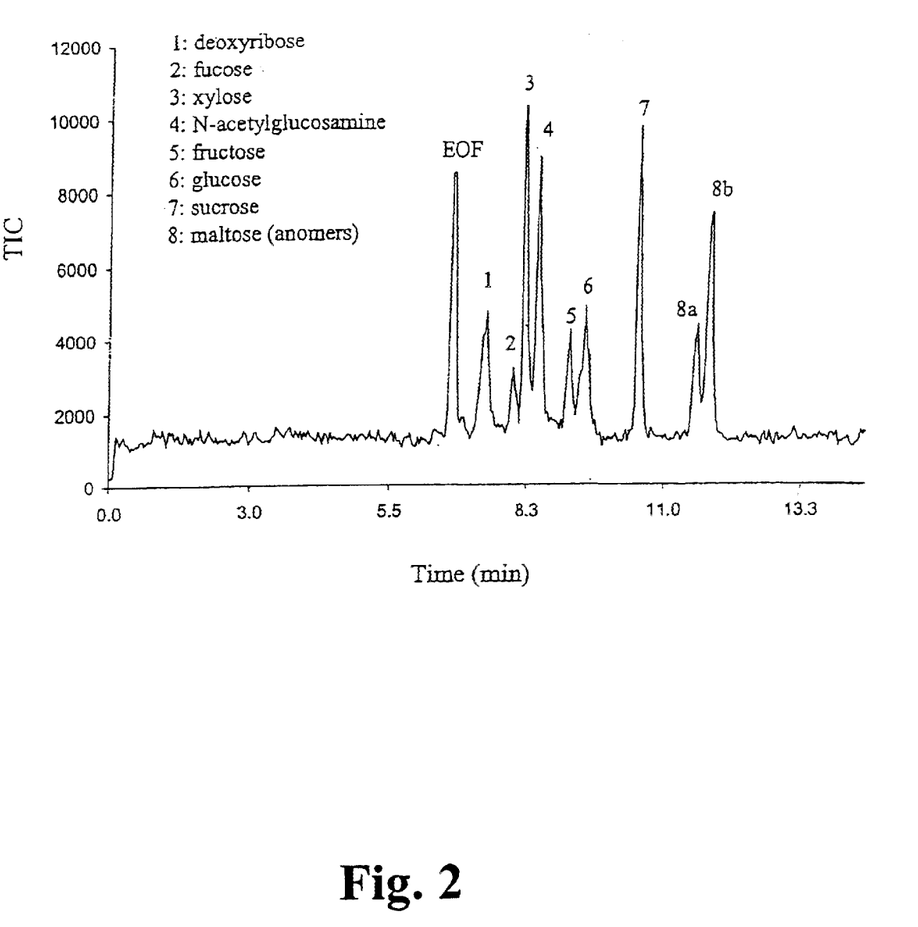
FIG. 2 is an electrochromatogram of a mixture of mono- and disaccharides separated on a cyano-phase CEC column.
Figure 3:
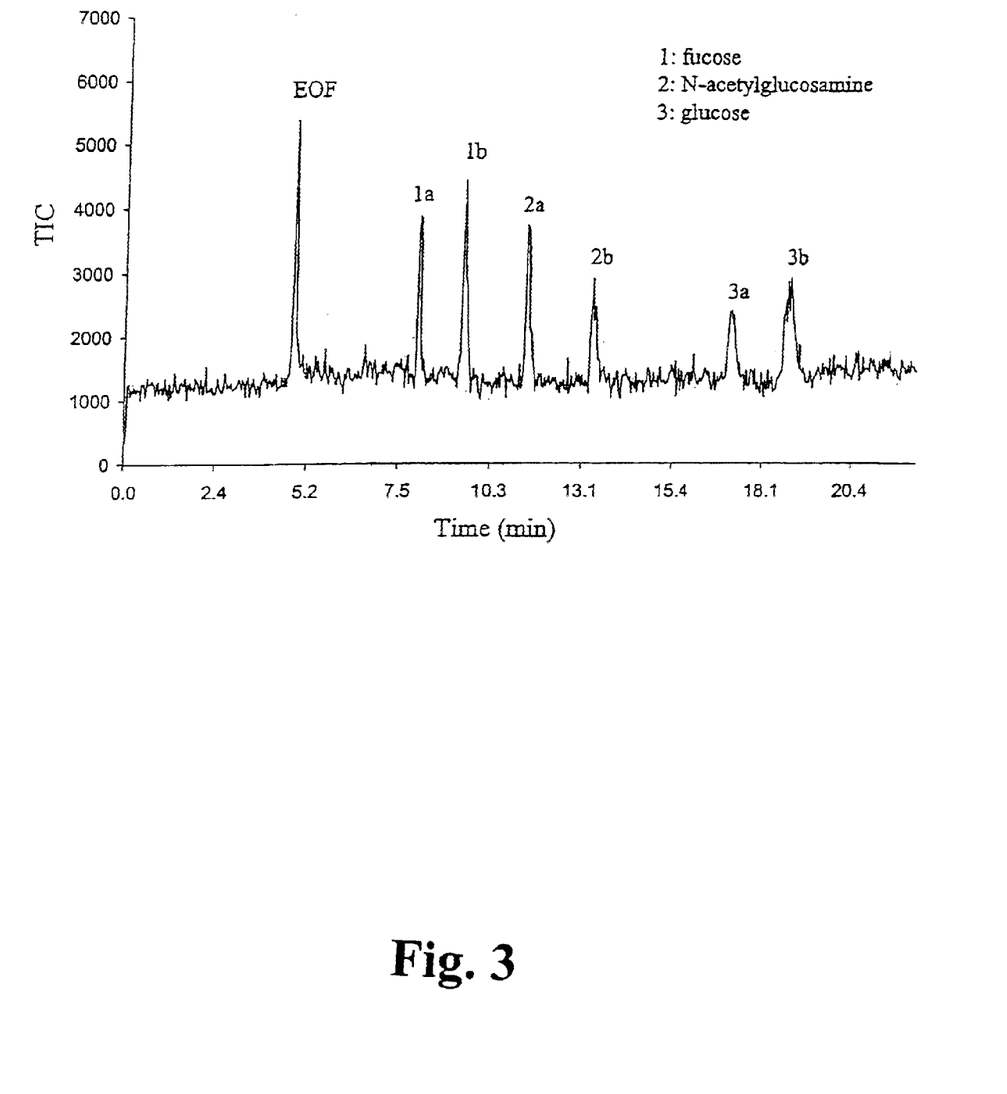
FIG. 3 is an electrochromatogram of a mixture of anomeric monosaccharides separated on a cyano-phase CEC column.

CEC Separation Attributes. FIG. 2 shows a separation of mono- and disaccharides on a cyano-phase CEC column (27 cm in length) with a mobile phase of acetonitrile/water/ammonium formate buffer (240 mM, pH 3.0), 76:23:1 (v/v/v). The conditions for separation were a field strength of 500 V/cm, an injections of 4 kV for 10 s. The following elution order was observed: deoxyribose; fucose; xylose; Nacetylglucosamine; fructose; glucose; sucrose; maltose. While not wishing to be bound by theory, this elution order reflects the hydrogen-bonding interaction mechanism: sugars with fewer hydroxy groups elute earlier than those containing more hydroxy groups, while ketoses elute earlier than aldoses and a hexosamine elutes earlier than hexose because the NH group has a weaker interaction with a polar stationary phase. At this mobile-phase condition, maltose (a reducing disaccharide) splits into two peaks because of its anomericity ($\alpha$ and $\beta$) due to mutarotation. Sucrose is a nonreducing sugar, displaying only a single peak. Considering the tradeoff between resolution and the appearance of anomers, the separation was optimized using the aforementioned mobile phase. As seen in FIG. 3, the resolution of anomers can be increased by using a higher content of organic solvent in the mobile phase (acetonitrile/water/ammonium formate buffer (240 mM, pH 3.0), 95:4:1, v/v/v), albeit at the expense of resolving all monosaccharides in a chromatogram.

At 95% acetonitrile in the mobile phase, three pairs of the anomeric monosaccharides formed through mutarotation were easily separated (FIG. 3). It appears more difficult to separate the anomeric monosaccharides than the oligosaccharides due to the requirement of a higher organic solvent content in the mobile phase.

The anomeric separations deserve a brief description. While deemed generally undesirable in the analysis of complex mixtures (e.g., oligosaccharides released from glycoproteins), the resolution of $\alpha$- and $\beta$-forms is beneficial in mutarotation studies. Due to the relatively low efficiency of HPLC (when compared to CEC in the present invention), only a band broadening and peak splitting were typically observed with conventional, bonded-phase columns. Certain conditions for resolving the anomers in HPLC even required the column temperatures in the range of 0–4° C., while maintaining a very high organic content (90:10) of the mobile phase. In contrast, under the CEC conditions used herein, the anomeric resolution becomes generally easy due to the combination of high efficiency and phase selectivity (FIGS. 3 and 4).

Figure 4:
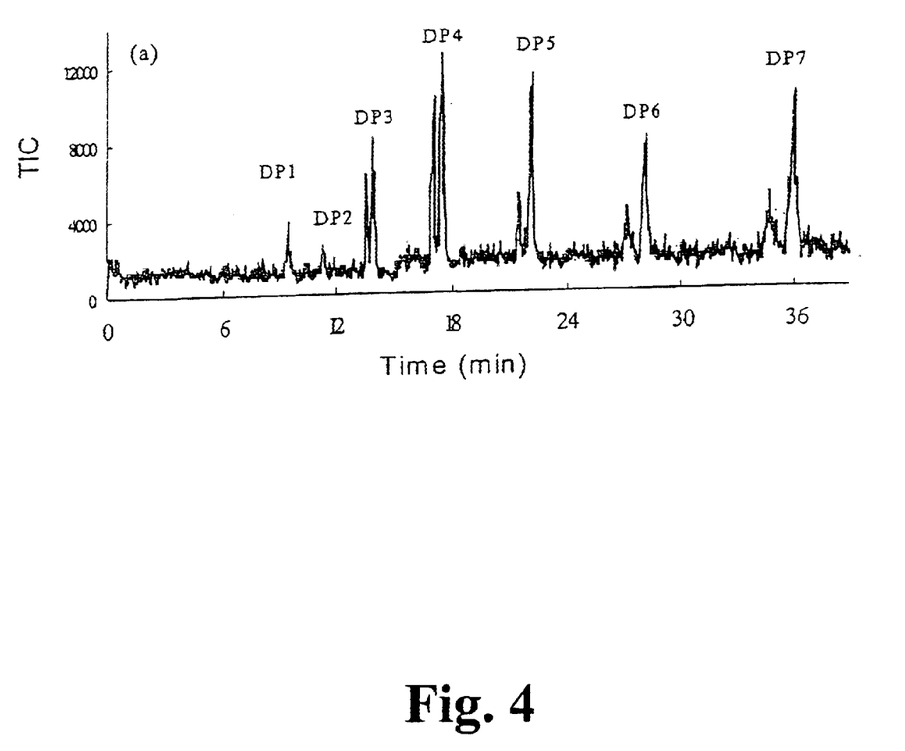
FIG. 4 is an electrochromatogram showing the separation of anomeric maltooligosaccharides from Dextrin 20 on an aminoalkyl-phase CEC column.

FIG. 4 demonstrates a mass electrochromatogram of the mixture of dextrin oligosaccharides (DP1–DP7) using 70% acetonitrile as the mobile phase (acetonitrile/water/ammonium formate buffer (240 mM, pH 3.0), 70:29:1). The column was an aminoalkyl-phase CEC column (28 cm long) developed with a field strength of 500 V/cm and an injection of 1 kV for 10 s. Each oligosaccharide displayed a pair of peaks due to mutarotation, except for DP1 and DP2. The column efficiency was ~200 000 theoretical plates/m. The separated pairs yielded identical spectra, since MS does not readily differentiate isomeric sugars such as anomers.

Figure 5:
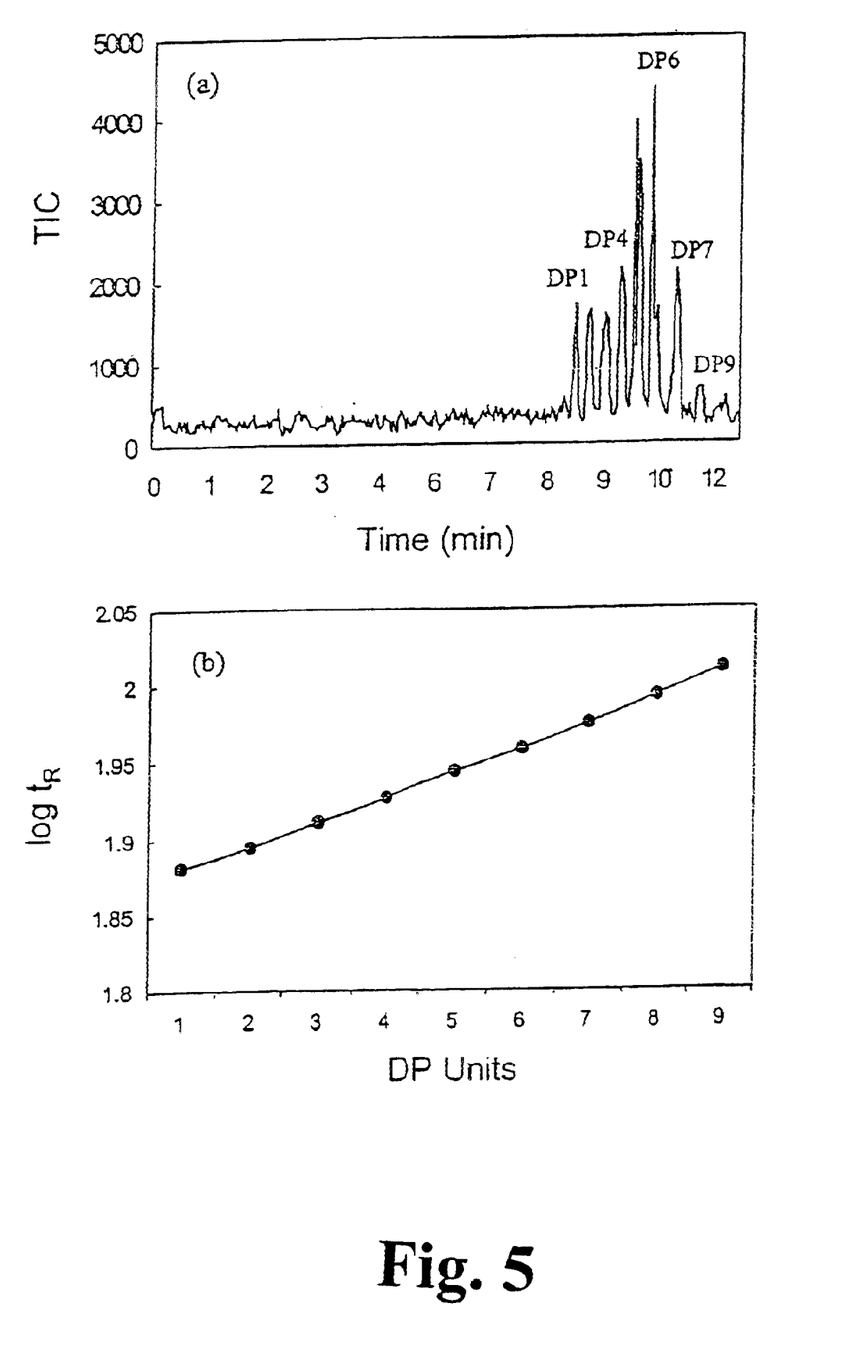
FIG. 5A is an electrochromatogram showing the separation of maltooligosaccharides from Dextrin 20 on an aminoalkyl-phase CEC column.
FIG. 5B is a graph showing the relationship between log $t_R$ and DP of linear maltooligomers.

For elimination of the peak-splitting phenomenon, the literature accounts suggested addition of 0.1% triethylamine to the mobile phase or an increase in column temperature to increase the rate of mutarotation. Verzele, M. et al., *J. Chromatogr.* 362, 23–31 (1986); Abott, S. R., *J. Chromatogr.* 18, 540–550 (1980). In the CEC experiments described herein, the amine addition was not found effective. It did not eliminate peak doublets but did increase the background and column instability. Therefore, we have the option of either separating the anomers at high resolution (shown in FIG. 4) or having the anomers elute together (as shown in FIG. 5a), depending on the composition of the mobile phase.

To mimic more closely the separation conditions suitable for profiling unknown oligosaccharide mixtures without anomeric separation, the percentage of acetonitrile in the mobile phase was reduced to 60% (acetonitrile/water/ammonium formate buffer (240 mM, pH 3.0), 60:39:1, v/v/v) when the model maltodextrin oligosaccharide mixture (DP=1–9) was used as a sample. The separation of this mixture (without peak splitting) is shown in FIG. 5A, and FIG. 5B demonstrates that the oligosaccharides are eluted in the order of their increasing molecular size. There is a linear relationship between the log $t_R$ (retention time) and the degree of polymerization, suggesting a hydrophilic-phase separation mechanism. A similar relationship was found earlier by Koizumi, K et al., *J. Chromatogr.* 409, 396–403 (1987) in the bonded-phase HPLC using a polar substrate.

Figure 6:
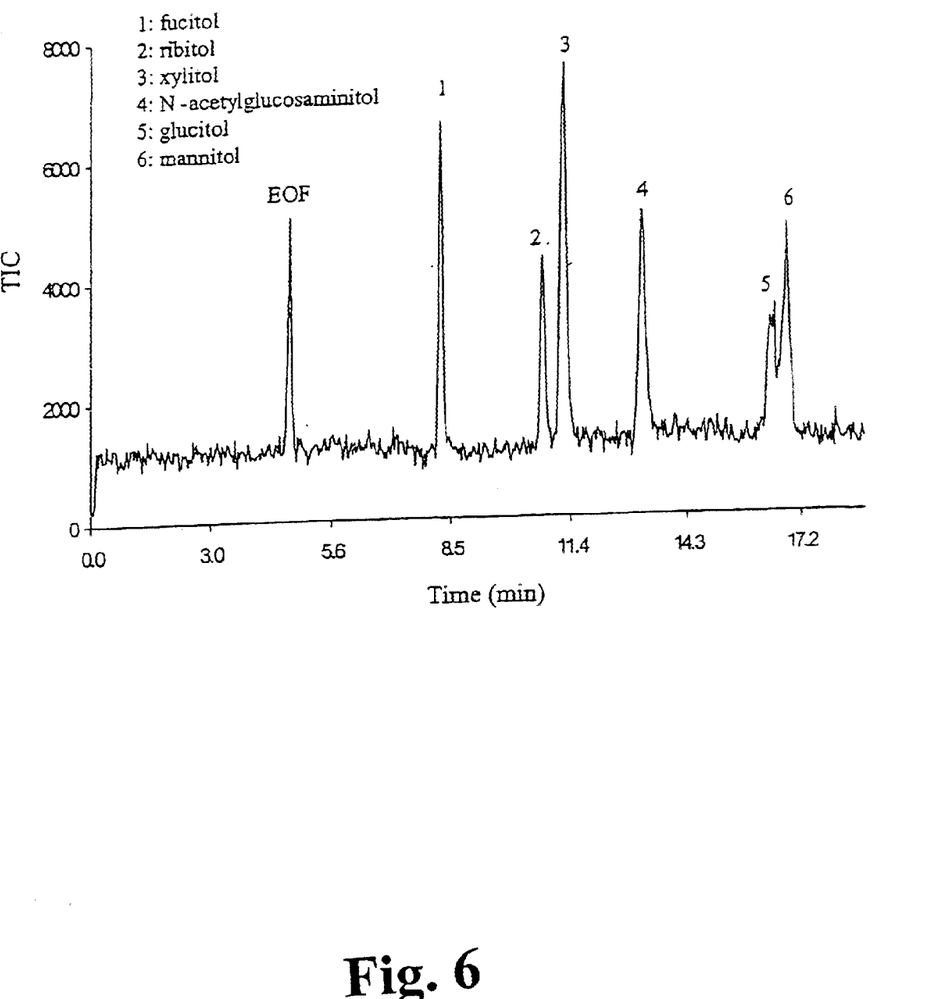
FIG. 6 is an electrochromatogram of a mixture of monosaccharide alditols separated on a cyano-phase CEC column.

Separation of Sugars as Alditols. When the saccharides with a reducing end are converted to their corresponding alditols, the problems associated with peak splitting are virtually eliminated. A direct conversion to alditols also occurs when oligosaccharides are cleaved through a $\beta$-elimination from glycoproteins, which has important consequences in glycoprotein analyses. Huang, Y. et al., *Anal. Chem.* 73, 6063–6069 (2001); Huang, Y. et al., *Rapid Commun. Mass Spectrom.* 16, 1199–1204 (2002). Therefore, the behavior of alditol mixtures in the CEC-based procedures was investigated. FIG. 6 shows the separation of some monosaccharide alditols: fucitol, ribitol, xylitol, N-acetylglucosaminitol, glucitol, and mannitol. Ribitol/xylitol and glucitol/mannitol are two pairs of epimers, which were separated in 95% acetonitrile as a mobile phase. Here, epimers are the sugar molecules that differ in configuration at just one of the several chiral centers. An earlier elution of ribitol before xylitol and glucitol before mannitol suggests that the hydroxy groups in xylitol and mannitol are less crowded, having better accessibility to interact with the stationary phase.

Figure 7:
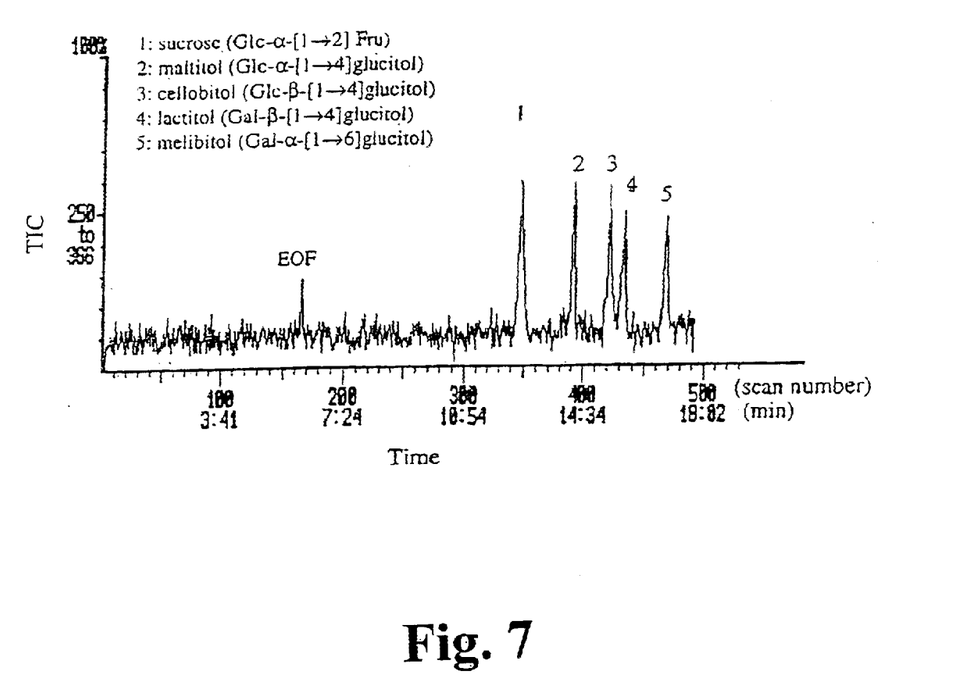
FIG. 7 is an electrochromatogram of a mixture of disaccharide alditols separated on a cyano-phase CEC column.

The isomeric disaccharide alditols, such as maltitol, cellobitol, lactitol, and melibitol, were completely resolved in the mobile phase containing 80% acetonitrile (acetonitrile/water/ammonium formate buffer (240 mM, pH 3.0), 80:19:1, v/v/v)(FIG. 7). Maltitol (Glc-$\alpha$[1→4]glucitol) and cellobitol (Glc-$\beta$[1→4]glucitol) are linkage isomers, while cellobitol (Glc-$\beta$[1→4]glucitol) and lactitol (Gal-$\beta$[1→4]glucitol) are compositional isomers. The disaccharide alditols were produced from the reaction of corresponding aldoses with sodium borohydride. Sucrose is a nonreducing aldose, thus eluting earlier than alditols.

Column Performance Characteristics. Both the amino-phase and cyano-phase CEC columns were investigated for the separation of various saccharide mixtures. During the course of the studies, it was found that the cyano-phase CEC columns were substantially more stable that the amino-phase below 6.4% for the column efficiencies. Cyano columns could last for ~50 successive injections without a loss of efficiency.

TABLE 1

Reproducibility of Retention and Efficiency[a]

| solute | $t_R$ (min) | RSD (%) | k | RSD (%) | plates/m | RSD (%) |
|---|---|---|---|---|---|---|
| Run-to-Run (n = 6) | | | | | | |
| fucitol | 7.92 | 1.5 | 0.22 | 2.3 | 246 540 | 2.7 |
| N-acetylglucosaminitol | 8.80 | 2.0 | 0.36 | 1.1 | 206 570 | 2.0 |
| glucitol | 9.85 | 1.3 | 0.51 | 1.8 | 225 870 | 3.4 |
| Column-to-Column (n = 6) | | | | | | |
| fucitol | 8.15 | 2.1 | 0.22 | 2.0 | 247 750 | 6.4 |
| N-acetylglucosaminitol | 9.05 | 2.1 | 0.35 | 1.4 | 203 200 | 2.1 |
| glucitol | 9.99 | 2.1 | 0.50 | 1.1 | 229 910 | 5.2 |

[a]Conditions: cyano columns, 27 cm in length; mobile phase, acetonitrile/water/ammonium formate buffer (240 mM, pH 3.0) 80:19:1 (v/v/v); field strength, 500 V/cm; injection, 4 kV for 10 s; sample concentration, 0.4 mg/mL for each sugar.

columns, presumably due to deterioration from the on-column Schiff base formation with the latter.

Figure 8:
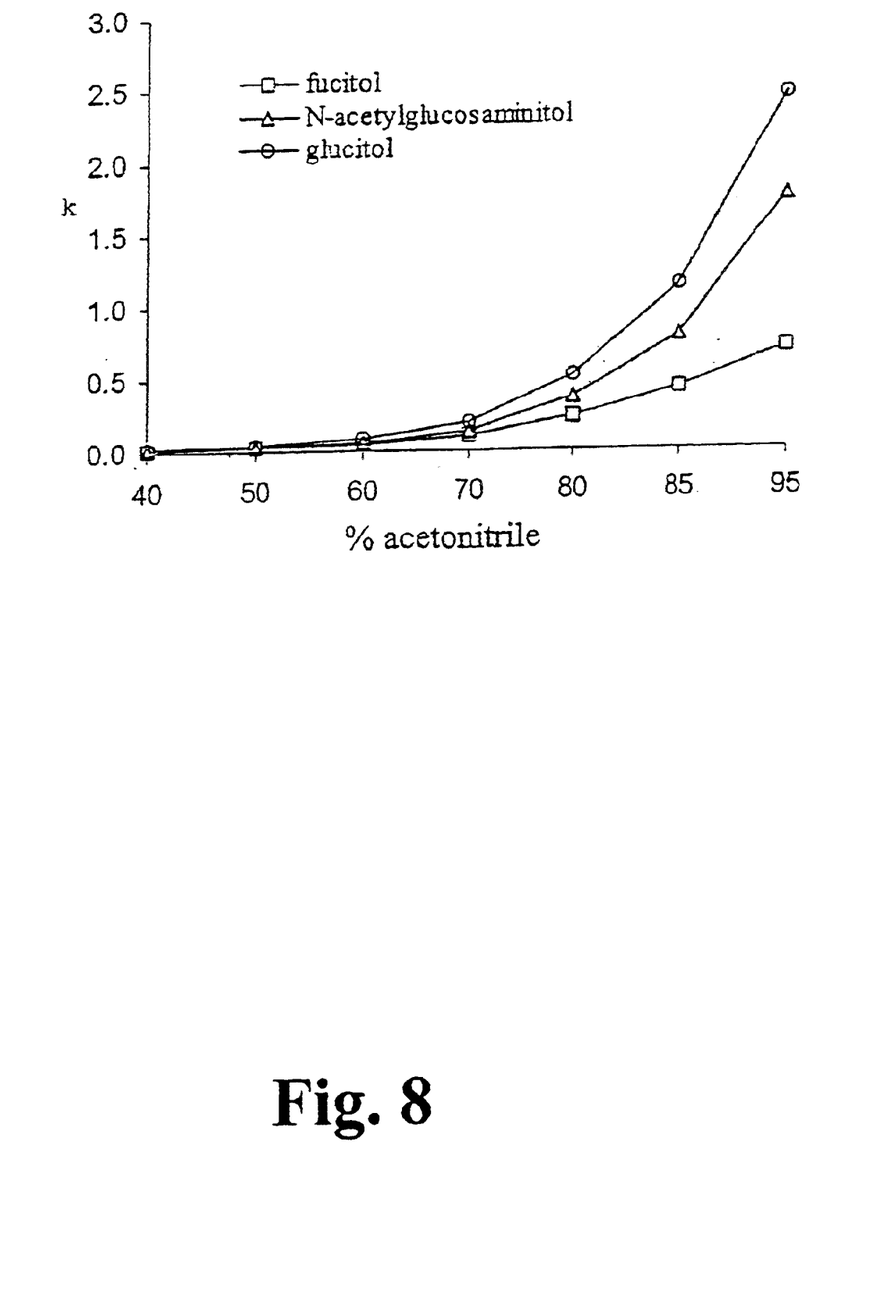
FIG. 8 is a graph showing the effect of mobile-phase composition on the separation factor, k.

Both the cyano-phase and amino-phase columns separate carbohydrate mixtures according to the normal-phase mechanism: (a) retention increases with the polarity of solutes (abundance of hydroxy groups); and (b) it increases when more acetonitrile is added to the mobile phase. As shown in FIG. 8, the capacity factor for three model alditols increased concomitantly with the percentage of acetonitrile in the mobile phase for the cyano stationary phase. It was found that CEC columns can tolerate up to 100% acetonitrile as the mobile phase without any adverse effects on column performance.

The applied voltage was found to directly influence the electroosmotic flow (EOF), as predicted and measured using an unretained marker, dimethyl sulfoxide, for velocity measurements. This relationship was strictly linear.

Figure 9:
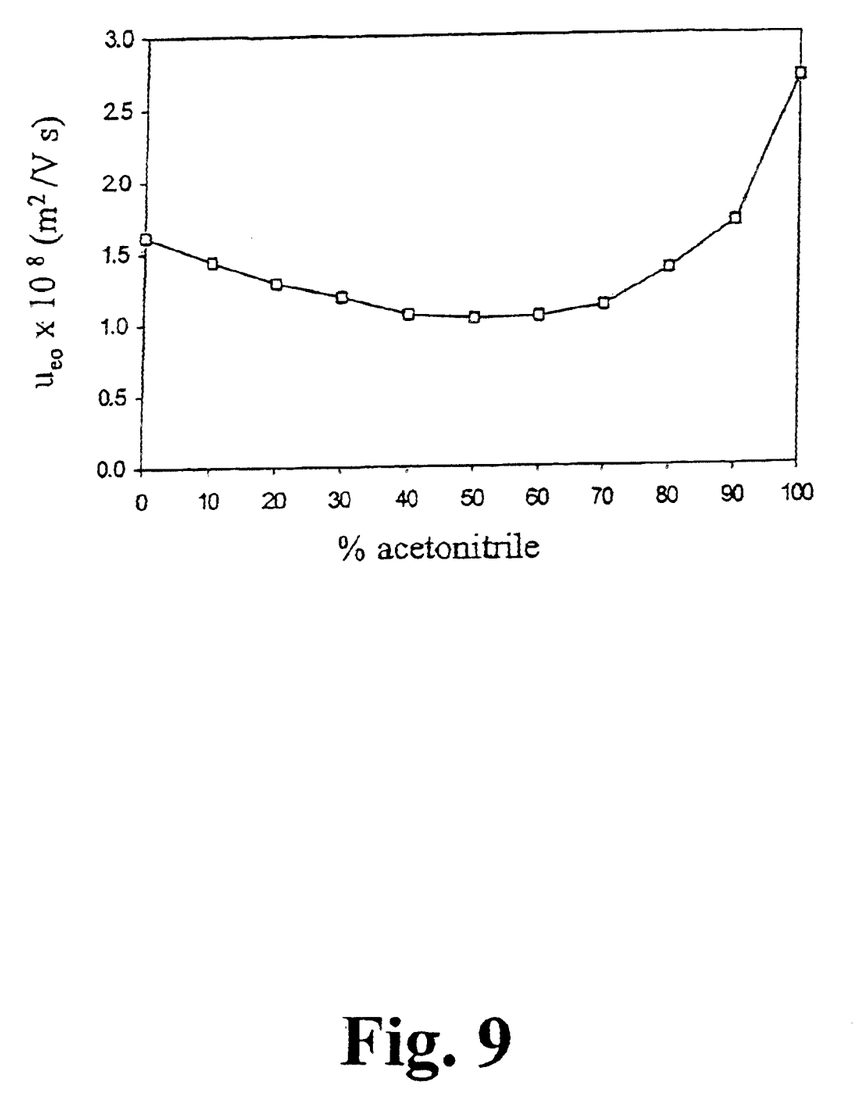
FIG. 9 is a graph showing the effect of acetonitrile percentage in the mobile phase on EOF.

FIG. 9 illustrates the dependency of electroosmotic mobility on the percentage of organic solvent (acetonitrile). The results show that increasing the percentage of organic solvent in the mobile phase up to 50% decreased the EOF. When the composition of the mobile phase was 50–60% organic solvent, EOF was minimal. As the mobile phase becomes pure acetonitrile, EOF increased. From the von Smoluchowski equation, (Bartle, K. D. et al., *J. Chromatogr., A* 916, 3–23 (2001) electroosmotic mobility $\mu_{eo}$ is inversely proportional to the viscosity of the mobile phase. The viscosity of an organic/water mixture is higher than that of pure water or pure organic solvent, thereby increasing electroosmotic mobilities $\mu_{eo}$ in pure water or organic solvent. Since the viscosity of acetonitrile is smaller than that of water, the mobility $\mu_{eo}$ in acetonitrile was higher than that in pure water.

To use the CEC columns effectively in the analysis of complex oligosaccharide mixtures, a high separation efficiency is required together with good reproducibility and column stability. Table 1 summarizes the evaluation of six successively prepared cyano monolithic columns. The retention times ($t_R$), separation capacity factors (k), and column efficiencies (plates/m) were evaluated for a test mixture of fucitol, N-acetylglucosaminitol, and glucitol. As shown in the table, the relative standard deviations (RSD) were more favorable for the run-to-run evaluations than the column-to-column measurements. Typical RSD values were found below 2.3% for the retention times and capacity factors and

CONCLUSIONS

Due to a unique combination of high efficiency (plate numbers) and chromatographic selectivity, CEC is eminently suited to deal with complex mixtures of glycans. CEC polar phases appear capable of resolving isomeric saccharides with the use of acetonitrile aqueous mobile phases. The mobile-phase composition used with these columns permits nearly ideal conditions for coupling with mass spectrometers for detection and identification of the individually separated glycans.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

What is claimed is:

1. A hydrophilic, monolithic chromatographic column including, as a stationary phase, a polyfunctional polyacrylamide gel, said polyacrylamide gel formed by polymerization of a monomer mixture, said mixture comprising acrylamide;
   bisacrylamide;
   a non-reactive filler compound for forming pores in the polyacrylamide gel;
   a polymerizable charge ligand of the formula RX wherein X is a functional group capable of maintaining a charge and R is an olefin functional group capable of free radical propagated polymerization; and
   a polymerizable cyano compound of the formula R'CN wherein CN is cyano and R' is an olefin functional group capable of free radical propagated polymerization.

2. The column of claim 1 wherein the charge ligand has a negative charge.

3. The column of claim 2 wherein the charge ligand is a sulfonic acid.

4. The column of claim 1 wherein the charge ligand has a positive charge.

5. The column of claim 4 wherein the charge ligand is a quaternary amine.

6. The column of claim 1 wherein the charge ligand is from about 5 mol % to about 40 mol % of the total monomer components of the mixture.

7. The column of claim 1 wherein the filler compound is polyethylene glycol.

8. The column of claim 7 wherein the polyethylene glycol has a molecular weight from about 7,500 to about 20,000.

9. The column of claim 1 wherein the filler compound is from about 1% (w/v) to about 5% (w/v) of the monomer mixture.

10. The column of claim 1 wherein the monomer R'CN forms about 30 mol % to about 40 mol % of the total monomer components of the mixture.

11. The column of claim 1 wherein R' of the monomer R'CN comprises an acrylate or a vinyl ether.

12. The column of claim 11 wherein the monomer R'CN of the monomer mixture is 2-cyanoethyl acrylate.

* * * * *